(12) United States Patent
Terwilliger et al.

(10) Patent No.: US 8,066,627 B2
(45) Date of Patent: Nov. 29, 2011

(54) DELIVERY SYSTEM AND METHOD FOR INTERSTITIAL RADIATION THERAPY USING STRANDS CONSTRUCTED WITH EXTRUDED STRAND HOUSINGS

(75) Inventors: Richard A. Terwilliger, Venice, CA (US); Gary A. Lamoureux, Woodbury, CT (US)

(73) Assignee: Biocompatibles UK Limited, Farnham, Surrey (GB)

( * ) Notice: Subject to any disclaimer, the term of this patent is extended or adjusted under 35 U.S.C. 154(b) by 1088 days.

(21) Appl. No.: 11/455,305

(22) Filed: Jun. 16, 2006

(65) Prior Publication Data
US 2006/0235365 A1 Oct. 19, 2006

Related U.S. Application Data

(63) Continuation of application No. 10/162,006, filed on Jun. 4, 2002, now Pat. No. 7,074,291.

(60) Provisional application No. 60/336,329, filed on Nov. 2, 2001, provisional application No. 60/360,272, filed on Feb. 26, 2002.

(51) Int. Cl.
*A61M 36/00* (2006.01)
*A61M 36/04* (2006.01)

(52) U.S. Cl. .......................... 600/8; 600/7
(58) Field of Classification Search .......... 600/1–8; *A61N 5/00, 5/01*
See application file for complete search history.

(56) References Cited

U.S. PATENT DOCUMENTS

| | | |
|---|---|---|
| 1,578,945 A | 3/1926 | Withers |
| 2,067,589 A | 1/1937 | Antrim |
| 2,153,889 A | 4/1939 | Frederick |
| 2,575,138 A | 11/1951 | Slaughter |
| 2,668,162 A | 2/1954 | Lowe |
| 2,703,316 A | 3/1955 | Schneider |
| 2,758,987 A | 8/1956 | Salzberg |
| 3,187,752 A | 6/1965 | Glick |
| 3,297,033 A | 1/1967 | Schmitt et al. |
| 3,351,049 A | 11/1967 | Lawrence |
| 3,565,869 A | 2/1971 | De Prospero |
| 3,636,956 A | 1/1972 | Schneider |

(Continued)

FOREIGN PATENT DOCUMENTS

EP 0 030 822 B1 9/1983

(Continued)

OTHER PUBLICATIONS

Merrick et al., "Seed Fixity in the Prostate/Periprostatic Region Following Brachytherapy," IJROBP vol. 46(1):pp. 215-220 (2000).

(Continued)

*Primary Examiner* — Charles A Marmor, II
*Assistant Examiner* — Catherine E Burk
(74) *Attorney, Agent, or Firm* — Fliesler Meyer LLP

(57) ABSTRACT

A delivery system and method for interstitial radiation therapy comprising substantially axially stiff and longitudinally flexible elongated members made of material which is bioabsorbable in living tissue and a plurality of radioactive seeds dispersed in a predetermined array within the elongate member. The radioactive seeds can be dispersed within assembled half-shells made of the same material. The housing for the radiation seeds can also be manufactured from extruded material. A system for manufacturing the interstitial radiation therapy seed strands that automatically makes the seed strands at the patient's bedside. The delivery system and method further customize the member based on a prescription.

34 Claims, 5 Drawing Sheets

U.S. PATENT DOCUMENTS

| | | |
|---|---|---|
| 3,752,630 A | 8/1973 | Takagi |
| 3,811,426 A | 5/1974 | Culver et al. |
| 3,839,297 A | 10/1974 | Wasserman et al. |
| 3,936,414 A | 2/1976 | Wright et al. |
| 4,052,988 A | 10/1977 | Doddi |
| 4,086,914 A | 5/1978 | Moore |
| 4,141,087 A | 2/1979 | Shalaby et al. |
| 4,167,179 A | 9/1979 | Kirsch |
| 4,402,308 A | 9/1983 | Scott |
| 4,416,308 A | 11/1983 | Bower |
| 4,416,659 A | 11/1983 | Simpson et al. |
| 4,441,496 A | 4/1984 | Shalaby et al. |
| 4,452,973 A | 6/1984 | Casey et al. |
| 4,473,670 A | 9/1984 | Kessidis |
| 4,509,506 A | 4/1985 | Windorski et al. |
| 4,510,295 A | 4/1985 | Bezwada |
| 4,612,923 A | 9/1986 | Kronenthal |
| 4,646,741 A | 3/1987 | Smith |
| 4,689,424 A | 8/1987 | Shalaby et al. |
| 4,697,575 A | 10/1987 | Horowitz |
| 4,702,228 A | 10/1987 | Russell et al. |
| 4,741,337 A | 5/1988 | Smith |
| 4,754,745 A | 7/1988 | Horowitz |
| 4,772,287 A | 9/1988 | Ray et al. |
| 4,784,116 A | 11/1988 | Russel, Jr. et al. |
| 4,815,449 A | 3/1989 | Horowitz |
| 4,847,505 A | 7/1989 | Suthanthiran |
| 4,891,165 A | 1/1990 | Suthanthiran |
| 4,916,209 A | 4/1990 | Fung et al. |
| 4,936,823 A | 6/1990 | Colvin et al. |
| 4,946,435 A | 8/1990 | Suthanthiran et al. |
| 5,022,940 A | 6/1991 | Mehoudar |
| 5,242,373 A | 9/1993 | Scott et al. |
| 5,264,540 A | 11/1993 | Cooper et al. |
| 5,339,812 A | 8/1994 | Hardy et al. |
| 5,391,139 A * | 2/1995 | Edmundson ................ 600/7 |
| 5,397,816 A | 3/1995 | Reilly et al. |
| 5,403,576 A | 4/1995 | Lin et al. |
| 5,405,309 A | 4/1995 | Carden, Jr. |
| 5,460,592 A | 10/1995 | Langton et al. |
| 5,521,280 A | 5/1996 | Reilly et al. |
| 5,713,828 A | 2/1998 | Coniglione |
| 5,755,704 A | 5/1998 | Lunn |
| 5,761,877 A | 6/1998 | Quandt |
| 5,833,593 A | 11/1998 | Liprie |
| 5,860,909 A | 1/1999 | Mick et al. |
| 5,928,130 A | 7/1999 | Schmidt |
| 5,938,583 A | 8/1999 | Grimm |
| 6,007,475 A | 12/1999 | Slater et al. |
| 6,010,446 A | 1/2000 | Grimm |
| 6,039,684 A | 3/2000 | Ildstad et al. |
| 6,053,858 A | 4/2000 | Bueche et al. |
| 6,080,099 A | 6/2000 | Slater et al. |
| 6,086,942 A * | 7/2000 | Carden et al. ................ 427/5 |
| 6,099,457 A | 8/2000 | Good |
| 6,132,359 A | 10/2000 | Bolenbaugh |
| 6,132,677 A | 10/2000 | Ohriner |
| 6,132,947 A | 10/2000 | Honan et al. |
| 6,159,143 A | 12/2000 | Lennox |
| 6,163,947 A | 12/2000 | Coniglione |
| 6,200,255 B1 | 3/2001 | Yu |
| 6,200,256 B1 | 3/2001 | Weinberger |
| 6,200,258 B1 | 3/2001 | Slater et al. |
| 6,213,932 B1 | 4/2001 | Schmidt |
| 6,248,057 B1 | 6/2001 | Mavity et al. |
| 6,264,599 B1 | 7/2001 | Slater et al. |
| 6,264,600 B1 * | 7/2001 | Grimm ................ 600/7 |
| 6,273,851 B1 | 8/2001 | Slater et al. |
| 6,283,911 B1 | 9/2001 | Keren |
| 6,312,374 B1 | 11/2001 | von Hoffmann |
| 6,319,190 B1 | 11/2001 | Schmidt et al. |
| 6,327,490 B1 | 12/2001 | Spetz |
| 6,358,195 B1 * | 3/2002 | Green et al. ................ 600/7 |
| 6,360,116 B1 | 3/2002 | Jackson, Jr. et al. |
| 6,387,034 B1 | 5/2002 | Lee |
| 6,398,709 B1 | 6/2002 | Ehr et al. |
| 6,403,916 B1 | 6/2002 | Spooner et al. |
| 6,419,621 B1 | 7/2002 | Sioshansi et al. |
| 6,428,504 B1 | 8/2002 | Riaziat et al. |
| 6,436,026 B1 | 8/2002 | Sioshansi et al. |
| 6,438,401 B1 | 8/2002 | Cheng et al. |
| 6,450,937 B1 | 9/2002 | Mercereau et al. |
| 6,450,938 B1 | 9/2002 | Miller |
| 6,450,939 B1 | 9/2002 | Grimm |
| 6,454,696 B1 * | 9/2002 | Kindlein et al. ................ 600/7 |
| 6,471,631 B1 | 10/2002 | Slater et al. |
| 6,472,675 B2 | 10/2002 | White et al. |
| 6,474,535 B1 | 11/2002 | Shanks et al. |
| 6,482,178 B1 | 11/2002 | Andrews et al. |
| 6,497,646 B1 | 12/2002 | Candelaria et al. |
| 6,500,109 B2 | 12/2002 | Tokita et al. |
| 6,514,193 B2 | 2/2003 | Kaplan |
| 6,537,192 B1 * | 3/2003 | Elliott et al. ................ 600/1 |
| 6,537,193 B1 * | 3/2003 | Lennox ................ 600/3 |
| 6,539,247 B2 | 3/2003 | Spetz |
| 6,549,802 B2 | 4/2003 | Thornton |
| 6,554,760 B2 | 4/2003 | Lamoureux et al. |
| 6,561,967 B2 | 5/2003 | Schmidt |
| 6,569,076 B1 | 5/2003 | Larsen et al. |
| 6,572,525 B1 | 6/2003 | Yoshizumi |
| 6,572,527 B2 | 6/2003 | Steele, Sr. et al. |
| 6,575,888 B2 | 6/2003 | Zamora et al. |
| 6,585,633 B2 | 7/2003 | Vitali et al. |
| 6,595,908 B2 | 7/2003 | Loffler et al. |
| 6,599,231 B1 | 7/2003 | Elliott et al. |
| 6,612,976 B2 | 9/2003 | Rosenthal et al. |
| 6,616,593 B1 | 9/2003 | Elliott et al. |
| 6,616,594 B2 | 9/2003 | Fontayne et al. |
| 6,626,817 B2 | 9/2003 | Luth |
| 6,632,176 B2 | 10/2003 | McIntire et al. |
| 6,638,205 B1 | 10/2003 | Chan et al. |
| 6,638,206 B2 | 10/2003 | Green et al. |
| 6,639,237 B2 | 10/2003 | Pedersen et al. |
| 6,648,811 B2 | 11/2003 | Sierocuk et al. |
| 6,656,106 B2 | 12/2003 | Schmidt |
| 6,656,107 B1 | 12/2003 | Pedersen et al. |
| 6,669,621 B2 * | 12/2003 | O'Hara et al. ................ 600/7 |
| 6,669,622 B2 | 12/2003 | Reed et al. |
| 6,679,824 B1 * | 1/2004 | Reed et al. ................ 600/7 |
| 6,682,471 B2 | 1/2004 | Steele, Sr. et al. |
| 6,689,043 B1 | 2/2004 | McIntire et al. |
| 6,709,381 B2 | 3/2004 | Munro, III |
| 6,716,156 B2 | 4/2004 | Menuhr et al. |
| 6,719,242 B2 | 4/2004 | Floyd et al. |
| 6,723,037 B2 | 4/2004 | Hamazaki et al. |
| 6,723,052 B2 | 4/2004 | Mills |
| 6,726,617 B1 | 4/2004 | Schmidt |
| 6,746,661 B2 | 6/2004 | Kaplan |
| 6,749,554 B1 | 6/2004 | Snow et al. |
| 6,752,753 B1 | 6/2004 | Hoskins et al. |
| 6,755,775 B2 | 6/2004 | Kalas et al. |
| 6,761,680 B2 | 7/2004 | Terwilliger et al. |
| 6,786,858 B2 | 9/2004 | Terwilliger et al. |
| 6,790,170 B2 | 9/2004 | Moody et al. |
| 6,800,055 B2 | 10/2004 | Amols et al. |
| 6,805,898 B1 | 10/2004 | Wu et al. |
| 6,820,318 B2 | 11/2004 | Terwilliger et al. |
| 6,837,844 B1 | 1/2005 | Ellard et al. |
| 6,846,283 B2 | 1/2005 | Green et al. |
| 6,905,455 B2 | 6/2005 | Rapach et al. |
| 6,911,000 B2 | 6/2005 | Mick et al. |
| 6,926,657 B1 | 8/2005 | Reed et al. |
| 6,969,344 B2 | 11/2005 | Drobnik et al. |
| 6,989,543 B2 | 1/2006 | Drobnik et al. |
| 7,008,367 B2 | 3/2006 | Visscher et al. |
| 7,060,020 B2 | 6/2006 | Terwilliger et al. |
| 7,074,291 B2 | 7/2006 | Terwilliger et al. |
| 7,083,566 B2 | 8/2006 | Tornes et al. |
| 7,094,198 B2 | 8/2006 | Terwilliger et al. |
| 7,118,523 B2 | 10/2006 | Loffler et al. |
| 7,211,039 B2 | 5/2007 | Lamoureux et al. |
| 7,232,408 B1 * | 6/2007 | Fritz et al. ................ 600/3 |
| 7,267,643 B2 | 9/2007 | Koster et al. |
| 7,322,928 B2 | 1/2008 | Reed et al. |
| 7,497,818 B2 | 3/2009 | Terwilliger et al. |
| 2001/0047185 A1 | 11/2001 | Satz |
| 2002/0066824 A1 | 6/2002 | Floyd et al. |

| | | | |
|---|---|---|---|
| 2003/0084988 | A1 | 5/2003 | Terwilliger et al. |
| 2003/0092958 | A1 | 5/2003 | Terwilliger et al. |
| 2003/0181794 | A1 | 9/2003 | Rini et al. |
| 2003/0191355 | A1 | 10/2003 | Ferguson |
| 2004/0024453 | A1 | 2/2004 | Castillejos |
| 2004/0109823 | A1* | 6/2004 | Kaplan ................... 424/1.11 |
| 2004/0116767 | A1* | 6/2004 | Lebovic et al. ............ 600/7 |
| 2004/0158117 | A1 | 8/2004 | Drobnik et al. |
| 2004/0158118 | A1 | 8/2004 | Drobnik et al. |
| 2004/0225174 | A1* | 11/2004 | Fuller et al. ............. 600/1 |
| 2005/0049490 | A1 | 3/2005 | Mills |
| 2005/0261541 | A1 | 11/2005 | Henderson et al. |
| 2006/0052654 | A1 | 3/2006 | Drobnik et al. |
| 2006/0063960 | A1 | 3/2006 | Wissman et al. |
| 2006/0094983 | A1 | 5/2006 | Burbank et al. |
| 2006/0121080 | A1 | 6/2006 | Lye et al. |
| 2006/0177379 | A1 | 8/2006 | Asgari |
| 2007/0224234 | A1 | 9/2007 | Steckel et al. |
| 2007/0238983 | A1 | 10/2007 | Suthanthiran et al. |

FOREIGN PATENT DOCUMENTS

| | | |
|---|---|---|
| EP | 0 292 630 A | 11/1988 |
| EP | 0 466 681 B1 | 1/1992 |
| EP | 0 668 088 A | 8/1995 |
| EP | 0993 843 A | 4/2000 |
| EP | 1 240 920 A | 9/2002 |
| WO | WO 00/64538 | 2/2000 |
| WO | WO 00/61229 | 10/2000 |
| WO | WO 2008/106586 | 9/2008 |

OTHER PUBLICATIONS

Poggi et al., "Marker Seed Migration in Prostate Localization," IJROBP vol. 56(5):pp. 1248-1251 (2003).

Tapen et al., "Reduction of Radioactive Seed Embolization to the Lung Following Prostate Brachtherapy," IJROBP vol. 42(5):pp. 1063-1067 (1998).

Meiller, R., "Advances May Improve Prostate Cancer Treatment," Board of Regents of the University of Wisconsin System, http:www.news.wisc.edu/11899.html 3 pages (Dec. 1, 2005).

Alvaro Martinez, et al; "Sterilization of $^{125}$I Seeds Encased in Vicryl Sutures for Permanent Interstitial Implantation"; Intl. J. Radiation Oncology Biol. Phys. vol. 5, pp. 411-413; Pergamen Press Ltd., 1979.

Van't Riet, "Ultrasonically Guided Transperineal Seed Implantation of the Prostate: Modification of the Technique and Qualitative Assessment of Implants", Intl. J. Rad. One. Biol. Phys. 24(3): 555-558 (1992).

Middleton et al., "Synthetic Biodegradable Polymers as Medical Devices", Med. Plas. Biomat. (Mar. 1998).

http://investor.mentorcorp.com/news/20010122-32414.cfm, "Mentor Acquires Breakthrough Brachytherapy Technology" (Jan. 25, 2002).

Webster's II New Riverside University Dictionary, p. 191, 1984.

Medi-Physics brochure entitled I-125 Seeds. No. 6711, Medi-Physics, Inc. Arlington Heights Il. 60004, USA; Revised. Oct. 1999, 2 pages.

Medi-Physics brochure entitled I-125 Seeds. No. 7000; Medi-Physics, Inc. Arlington Heights Il. 60004, USA; Revised. Oct. 1999, 2 pages.

Amersham Health; "EchoSeed™"; http://www.amershamhealth-us.com/echoseed/ printed Nov. 19, 2003.

Amersham Health; "Rapid Strand Indications" Http;//www.amershamhealth-us.com/products/index.htp?a=i&i=38; printed Nov. 19, 2003.

Amersham Health; OncoSeed™ (Iodine-125 Seeds) http://www.amershamhealty-us.com/oncoseed/; printed Nov. 19, 2003.

RadioMed: Innovative Products for Radiation, "The Visicoil Advantage . . . for Image Guided Radiation Therapy," http://www.radiomed.com/visicoil/, at lease as early as Aug. 2003.

Oncura, "RapidStrandR$_x$: The Logical Choice for Improved Dosimetry," Ocura Inc., Plymouth Meeting, PA, Apr. 2005.

* cited by examiner

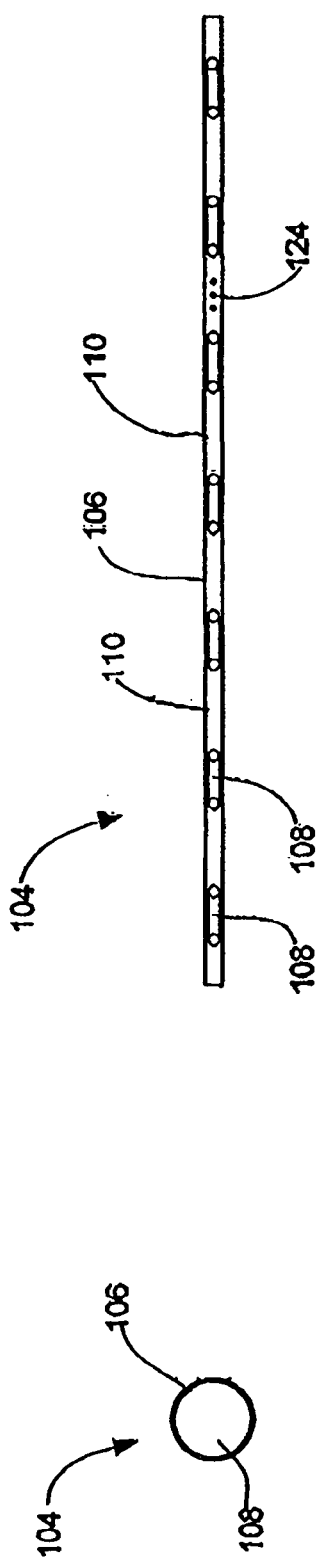
FIG. -1A
FIG. -1B
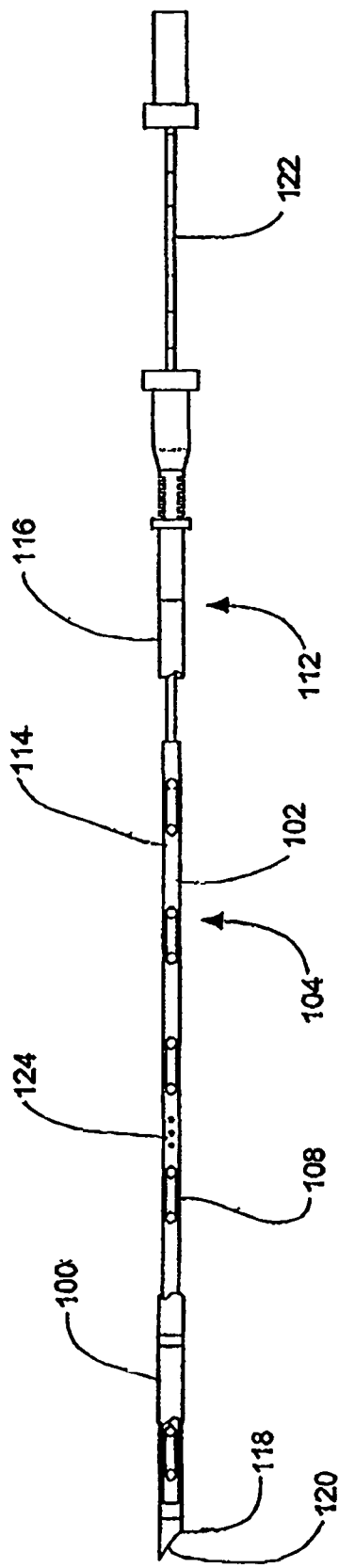
FIG. -1C

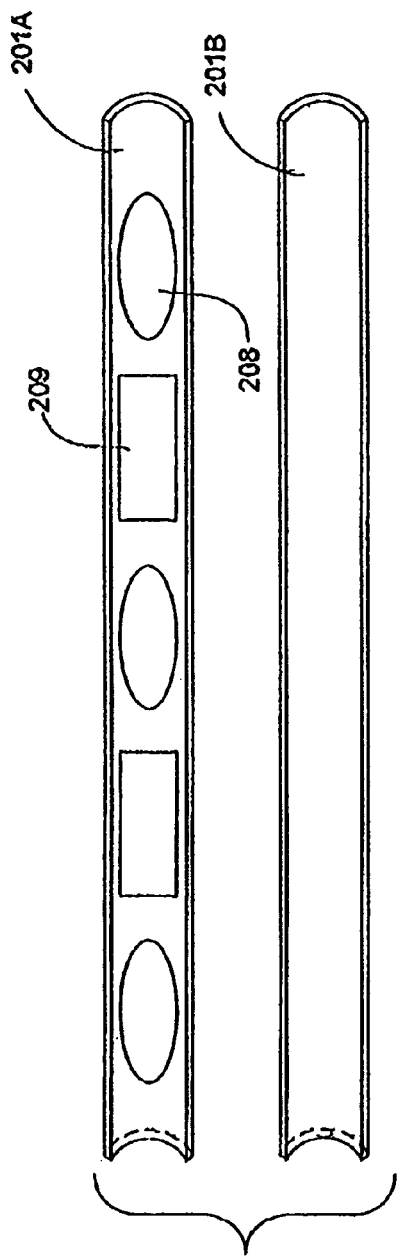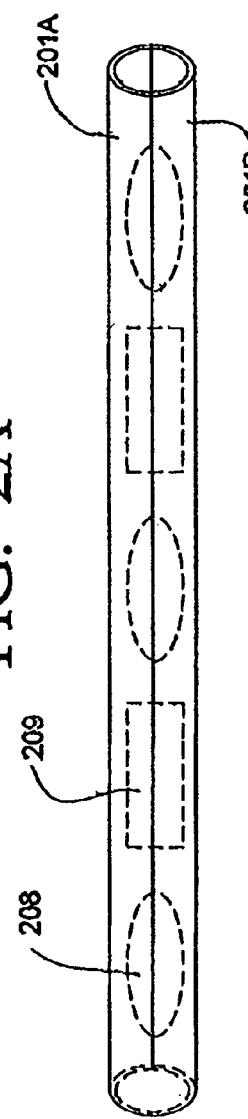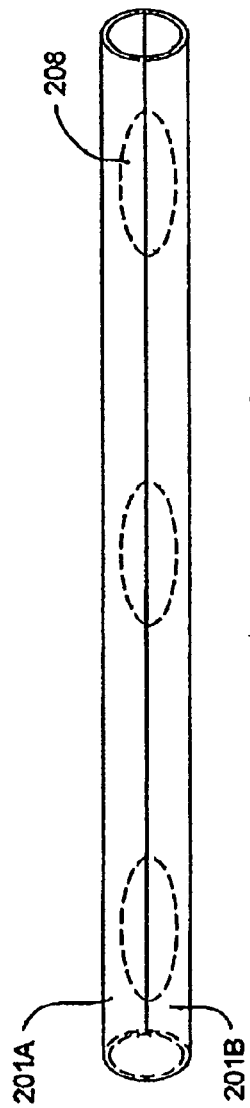
FIG. -2A
FIG. -2B
FIG. -2C

US 8,066,627 B2

DELIVERY SYSTEM AND METHOD FOR INTERSTITIAL RADIATION THERAPY USING STRANDS CONSTRUCTED WITH EXTRUDED STRAND HOUSINGS

CLAIM OF PRIORITY

This application is a continuation of U.S. patent application Ser. No. 10/162,006 (now allowed), filed Jun. 4, 2002, which claims priority under 35 U.S.C. §119(e) to U.S. Provisional Patent Application No. 60/336,329, filed Nov. 2, 2001 and U.S. Provisional Patent Application No. 60/360,272, file Feb. 26, 2002, each of which is incorporated herein by reference.

CROSS-REFERENCE TO RELATED APPLICATIONS

The following applications are cross-referenced and incorporated herein by reference:

U.S. Patent Application No. 60/360,241 entitled "Delivery System and Method for Interstitial Radiation Therapy Using Seed Strands Constructed With Preformed Strand Housing," by Terwilliger et al., filed Feb. 26, 2002.

U.S. Patent Application No. 60/360,321 entitled "System for Manufacturing Interstitial Radiation Therapy Seed Strands," by Terwilliger et al., filed Feb. 26, 2002.

U.S. Patent Application No. 60/360,299 entitled "Delivery System and Method for Interstitial Radiation Therapy Using Seed Elements With Ends Having One of Projections and Indentations," by Terwilliger et al., filed Feb. 26, 2002.

U.S. Patent Application No. 60/360,260 entitled "Delivery System and Method for Interstitial Radiation Therapy," by Terwilliger et al., filed Feb. 26, 2002.

FIELD OF INVENTION

The present invention relates to systems and methods for delivering a plurality of radioactive sources to a treatment site.

BACKGROUND

In interstitial radiation therapy, one method for treating tumors is to permanently place small, radioactive seeds into the tumor site. This method is currently accomplished by one of the following two procedures: (a) loose seeds are implanted in the target tissue, and/or (b) seeds are contained within a woven or braided absorbable carrier such as braided suture material and implanted in the target tissue. The loose seeds, however, are dependent on the tissue itself to hold each individual seed in place during treatment, and the woven or braided sutures do not assist in the placement of the seeds relative to the target tissue.

There have been many developments in brachytherapy (i.e. therapy relating to treating malignant tumors with such radioactive seeds). In one technique, hollow metal needles are inserted into the tumor and the seeds are thereafter inserted into the needles, while the needles are being retracted to deposit the seeds in the tumor at the desired locations. Such devices are shown in U.S. Pat. No. 4,402,308 which is incorporated herein by reference. The most commonly used instruments are the Henschke and Mick devices. The use of such devices has distinct disadvantages. The overall length of such devices is over 20 cm and such devices have significant weight making them difficult to manipulate.

Another disadvantage of the above technique is that the seeds are deposited in a track made by the needle. When the needle is withdrawn, there is a tendency for the seeds to migrate in that track resulting in a poor distribution of the seeds. Because the energy levels are low, distribution between centers of adjacent seeds should be on the order of about 1 cm for certain treatments. Poor distribution of seeds can result in undesirable concentrations of seeds resulting in either an over-dosage or an under-dosage of radiation. Additionally, over time, the seeds tend to migrate along the needle track, away from the tumor, and accordingly patients commonly must repeat the procedure within a couple months to have seeds re-implanted near the tumor.

Further complicating the procedure is the fact that the seeds are small, because they need to fit in small bore needles to prevent excessive tissue damage. Due to their small size and high seed surface dose, the seeds are difficult to handle and to label, and can easily be lost. In addition, the technique of implantation of individual seeds is time consuming.

One preferred method of introducing seeds into the tumor site is using a pre-manufactured elongated assembly or implant that contains seeds spaced between spacers at 1 cm increments. This assembly is capable of being loaded into an introducer needle just prior to the procedure. What is desired in using an elongated assembly of seeds and spacers is the ability to insert such an assembly into a tumor site to provide controlled and precise placement of the radioactive seeds.

While assemblies with bio-absorbable materials and spaced radioactive seeds are known for use as interstitial implants, such assemblies are not entirely satisfactory. In one instance, the elongated implant is made using a bio-absorbable material consisting of an Ethicon Vicryl®. This material is commonly known as PGA. Radioactive seeds and teflon spacers are inserted into the material. Needles loaded with the seeds in the carrier bio-absorbable material are sterilized or autoclaved causing contraction of the carrier material and resulting in a rigid column of seeds and spacers. This technique was reported in "Ultrasonically Guided Transperineal Seed Implantation of the Prostate: Modification of the Technique and Qualitative Assessment of Implants" by Van't Riet, et al., International Journal of Radiation Oncology, Biology and Physics, Vol. 24, No. 3, pp. 555-558, 1992 which is incorporated herein by reference. Such rigid implants have many drawbacks, including not having the ability to flex with the tissue over the time that the bio-absorbable material dissolves.

As the tissue or glands being treated shrink back to preoperative size, and thus as the tissue recedes, a rigid elongated implant does not move with the tissue, but remains stationary relative to the patient. The final location relative to the tumor is thus not maintained and the dosage of the radioactive seeds does not meet the preoperative therapy plan.

Another system for providing an elongated implant having radioactive seeds disposed therein is disclosed in U.S. Pat. No. 4,697,575 which is incorporated herein by reference. In this reference, a plurality of encapsulated radioactive seeds are positioned in a predetermined array. The seeds are encapsulated in individual capsules, with each capsule having a projection on one capsule end and a complementary recess on the remaining capsule end. A projection in one capsule is engageable with a recess in an adjacent capsule such that the desired number of seeds can be plugged together to form a column of rigid, bio-absorbable and elongated material. This implant is not entirely satisfactory inasmuch as it is time consuming and inefficient to carry out the manipulative steps of assembling such a strand of elongated material. Further the implant is quite rigid as it is inserted into a patient without the use of an introduction needle, as the implant itself acts as a rigid needle that is undesirably left in place.

In another embodiment disclosed in the above patent, a rigid needle implant containing radioactive segments, with break points, is inserted into the tumor. The needle implant is made of a bio-absorbable polymer that is rigid enough to be driven into the tumor without deflection and without the use of a separate hollow needle. When the proper depth is reached with the rigid polymer needle, the remaining, uninserted portion of the needle is broken off. This embodiment has the disadvantage of the above embodiment. As the implant is too rigid, the implant does not follow the tumor as it shrinks back to its normal size.

In U.S. Pat. No. 6,163,947, Coniglione, issued Dec. 26, 2000, and incorporated herein by reference, a string of hollow seeds described in U.S. Pat. No. 5,713,828, issued Feb. 3, 1998, also incorporated herein by reference, are strung onto a thin strand of suture material to form an array of seeds. This string of seeds is delivered into the tumor site placed within a hollow needle. Since the hollow lumen of the seeds are substantially smaller in diameter in relation to the outside diameter of the seed body, the string of suture material must be substantially smaller in diameter than the seeds themselves. The resulting diameter of the suture makes the suture axially weak and the suture can fold up between the seeds within the needle lumen as pressure is applied on the proximal end of the strand within the needle. Thus the difference in diameter between the seed and the thin suture material makes the assembly susceptible to collapse from axial force applied on the proximal end, resulting in jamming of the assembly within the needle lumen and/or the assembly not maintaining the proper desired spacing between radioactive seeds as the assembly is expelled into the treatment site.

One relevant reference discloses modification of the needle structure to include a reloadable cartridge. In such reference the needle is inserted and as a cartridge of seeds is emptied, the plunger of the device is withdrawn and a new cartridge containing radioactive seeds is loaded into the syringe (Moore, U.S. Pat. No. 4,086,914, issued May 2, 1978). Another reference offers a device for implanting individual seeds in a planar dispensing device with multiple needles to ensure accurate placement of the seeds relative to one another and the treatment site (Kirsch, U.S. Pat. No. 4,167,179 issued September 1979). Another reference disclosed a shielding devices for bead strands which prevents radiation exposure for health care personnel performing treatment with the radioactive seeds (Windarski, U.S. Pat. No. 4,509,506 issued April 1985). All of the above references are incorporated herein by reference.

In another technique for treating tumors disclosed in U.S. Pat. No. 5,460,592 and incorporated herein by reference, seeds are held in a woven or braided bio-absorbable carrier such as a braided suture. The carrier with the seeds laced therein is then secured in place to form a suitable implant. This braided assembly exhibits many drawbacks, as and when the braided assembly is placed into the tumor. The needle that carries the braided assembly must be blocked at the distal end to prevent body fluids from entering the lumen. If body fluid reaches the braided assembly while the assembly is still in the lumen of the needle, the braided assembly can swell and jam in the lumen. Because the assembly is made of a braided tubular material, it is difficult to push the assembly out of the needle. As the needle is withdrawn from the tumor, pressure on the proximal end of the braided assembly causes the braid to expand and jam inside the lumen of the needle. Finally, if the braided strand is successfully expelled from the needle, the relative spacing of the seeds may not be maintained, if the braided material has collapsed.

Another apparatus for automated production of brachytherapy devices is the Mentor Isoloader™. The Isoloader™ consists of an interface to commercial treatment planning systems, a shielded seed cartridge, a shielded needle cartridge, a shielded needle holder and a radiation detector for seed assay. The Isoloader™ picks the radioactive seeds, tests each one for radiation and then automatically loads the seed into a needle. The apparatus provides for automated loading and verification of radioactive seeds into needles. With the Isoloader™ system, the clinician plans the treatment for a specific patient using standard software, and orders brachytherapy seeds of a suitable quantity and activity level for that patient. The seeds are shipped to the clinician in a pre-sterilized cartridge with a memory chip containing the individual data and seed specifications. The cartridge is inserted into the Isoloader™, and the seeds are automatically loaded into the surgical needles according to the treatment plan. The Isoloader™ produces a rigid needle system that does not move with the tissue, as the tumor shrinks during treatment.

Other references that address such implants and materials include the following, all of which are incorporated herein by reference.

U.S. Patent Documents:
U.S. Pat. No. 1,578,945 issued January 1923 to Withers
U.S. Pat. No. 2,067,589 issued January 1937 to Antrim
U.S. Pat. No. 3,351,049 issued November 1967 to Lawrence
Medi-Physics brochure entitled "I-125 Seeds®. In Carrier", Model No. 6720.
Medi-Physics brochure entitled "I-125 Seed®. Source Model 6711".
Martinez et al., Int. J. Radiation Oncology Biol. Phys., vol. 5, No. 3, March 1979, pp. 411-413.

SUMMARY OF SOME OF THE ASPECTS OF THE INVENTION

Accordingly, the present invention cures and addresses the disadvantages exhibited in the prior art devices and implants. What is desired is to provide a bio-absorbable carrier material having seeds disposed within the material, with the seeds being accurately spaced a predetermined distance from one another, with the seeds repeatably maintaining that spacing, even after being introduced into the body.

It is further desired that an elongated member with seeds be sufficiently rigid axially to allow expulsion of the member while maintaining the spacing between seeds, and that the member be flexible and pliable enough to move with the tissue as the tissue shrinks back to pre-operative size.

Accordingly, some of the objectives of the present invention include providing an elongated member with seeds dispersed throughout, which obviates the aforementioned disadvantages and allows placement of the seeds in accurate positions to provide the desired interstitial radiation dose to the location derived from a preoperative dosimeter plan.

A further object of the present invention is to provide a delivery system for interstitial radiation therapy, which is faster and easier to use than prior art systems.

Another object of the present invention is a delivery system that causes a minimum of trauma to tissue.

Yet another object of the present invention is a delivery system that allows for control of the radiation dosage given the tissue. Still further objects of the present invention is a delivery system that can be used and placed with precision, and that maintains the position of the implant after the implantation, until the bio-compatible material dissolves and the seeds have become inert. In another aspect the bio-compatible material is selected to absorb about when the half-life of the radioactive seeds is reached.

A further aspect is to have the implant be echogenic.

In accordance with an embodiment of the invention, the delivery system comprises a substantially axially stiff and longitudinally flexible elongated member that is bio-absorbable in living tissue. The member has a length that greatly exceeds its width or diameter. The elongated member has a plurality of radioactive seeds dispersed therein in a predetermined array.

In another embodiment, the substantially axially stiff and radially flexible elongated member comprises a single continuous monofilament element of bio-compatible material that has a plurality of seed sources molded therein. The bio-compatible material can be preferably a bio-absorbable polymer or copolymer material that encapsulates the plurality of radioactive seeds.

A further embodiment of the invention is characterized as a substantially constant diameter elongated member of a bio-absorbable polymer with seeds positioned therein at predetermined spacing along its length, whose diameter is a close fit to the needle lumen, thus preventing collapse as axial force is applied on the proximal end of the elongated member. The space between the seed sources is maintained throughout the insertion and expulsion of the elongated member. The diameter of the polymer between the seeds may be slightly reduced in relation to the overall diameter of the elongated member, but is of sufficient diameter so as to not allow collapse of the member within the needle lumen.

The present embodiment of the invention further allows for variation in any spacing between seeds, as the semi-rigid, deflecting elongate member can be produced under a doctor's prescription for each patient, with optimal seed distribution for a particular patient's treatment program.

Thus an object of the invention is to provide an implant that can be custom made as specified by a prescription for an individual patient.

It is also desired that the present invention provide for elongate members shaped like half-shells. Radioactive or other seed elements and/or spacers can then be placed within one half-shell. The empty half-shell is then mated to the half-shell containing the seed elements or spacers, with the two half-shells now forming a tube structure that contains the seed elements and spacers. Then the half-shells are heated, causing them to fuse into a single therapeutic element and fixing the seeds and spacers within the therapeutic element. The resulting therapeutic element is axially rigid and radially flexible. Two half-shells can also be assembled as described above containing the seed elements and spacers and liquid material flowed into the assembled half-shell. The liquid material then solidifies, fusing the half-shells and fixing the seed elements and spacers inside. The solidified material is axially rigid and radially flexible and may be a bio-absorbable polymer.

In another embodiment, liquid polymer is flowed into a half-shell into which has previously been placed seeds. The polymer can solidify at the other half-shell is placed in contrast with the first half-shell. The assembly can be heated so the assembly fuses together.

Another object of the present invention is to provide a bedside apparatus that produces interstitial radiation therapy seed strands made of a material having seeds disposed within the material with the seeds being accurately spaced a predetermined distance from one another.

The present invention cures and addresses the disadvantages exhibited in the prior art devices, implants and manufacturing devices and methods. It is also desired to provide a device and method that extrudes a bio-absorbable carrier material into an elongate hollow member and loads seeds within the bore of the extruded material, during or after extrusion, with the seeds being accurately spaces a predetermined distance from one another, and the seeds repeatably maintaining that spacing, even after being introduced into the body.

Further aspects, objects, advantage and embodiment of the invention can be understood from the specification, the figures and the claims.

DESCRIPTION OF THE DRAWINGS

The Embodiments of FIGS. 1A through 1C Represent a Delivery System and Method for Interstitial Radiation Therapy FIG. 1A is an enlarged side view of an embodiment of the therapeutic implant of the invention.

FIG. 1B is an enlarged view of a cross-section of an embodiment of the therapeutic implant of the invention of FIG. 1.

FIG. 1C is an enlarged side view of the brachytherapy device including the implant of FIG. 1A.

The Embodiments of FIGS. 2A through 2E Represent a Interstitial Radiation Therapy Seed Strands Constructed with Half-Shell Strand Housings FIG. 2A is an enlarged side view of an embodiment of the half-shell and radioactive seed elements and spacers of the invention.

FIG. 2B is an enlarged side view of an embodiment of the assembled therapeutic implant of the invention similar to FIG. 2A.

FIG. 2C is an enlarged side view of another embodiment of the half-shells and radioactive seed elements of the invention.

The Embodiment of FIG. 3 is a System for Manufacturing Radiation Therapy Seed Strands

The Embodiment of FIGS. 4A through 4C is a System for Manufacturing Radiation Therapy Seed Strands Using Extruded Strand Housings

DETAILED DESCRIPTION OF THE PREFERRED EMBODIMENT

Figure 2D:
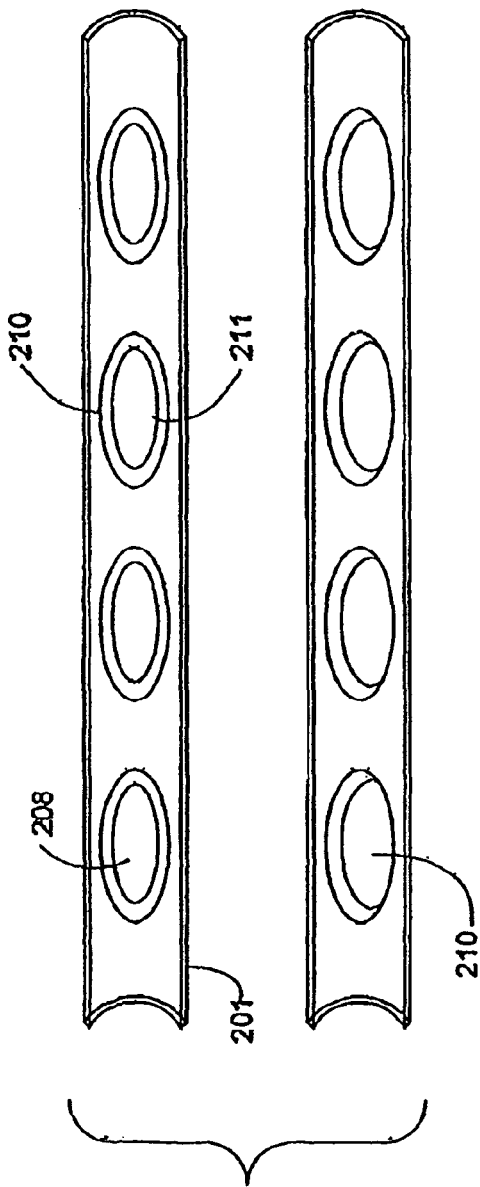
FIG. 2D is an enlarged side view of the brachytherapy device with two half-shells with indentations for seed elements.

In accordance with an embodiment of the invention, a substantially axially, semi-rigid and radially or laterally flexible elongated member made of material, which is bio-absorbable in living tissue, is provided for insertion in tumors. A plurality of radioactive seeds are encapsulated and positioned in a predetermined array in the member in the desired spaced relationships.

The seeds can be of various types having low energy and low half-life such as Iodine seeds, known as I-125 seeds, consisting of a welded titanium capsule containing iodine 125 absorbed on a silver rod, or Palladium 103 seeds. Examples of radioactive seeds used to manufacture the therapeutic element appear in Table 1 below.

TABLE 1

Seed Manufacturers and Common Types of Seeds.

| PART NUMBER | MANUFACTURER | SEED NAME |
|---|---|---|
| IODINE 125 | | |
| 80040-A | Amersham 6702 | OncoSeed |
| 80040-B | Amersham 6711 | RAPID Strand |
| 80040-C | North American Scientific | IoGold |
| 80040-D | Best Industries | BEST Iodine-125 |
| 80040-E | Bebig | Symmetra |
| 80040-F | Mills Biopharmaceuticals | ProstaSeed |
| 80040-G | Syncor | PharmaSeed |
| 80040-H | International Isotopes | IsoStar |
| 80040-I | Implant Sciences | I-Plant |
| 80040-J | International Brachytherapy | InterSource-125 |
| 80040-K | Source Tech | STM1251 |
| 80040-L | DRAXIMAGE, Inc. | BrachySeed |
| PALLADIUM 103 | | |
| 80035-A | North American Scientific | Pd Gold |
| 80035-B | Theragenics | Theraseed 200 |
| 80035-C | Best Industries | BEST Palladium-103 |
| 80035-D | International Brachytherapy | InterSource 103 |

Additionally, seeds can be manufactured using iridium 192, cesium 131, gold 198, yttrium 90 and phosphorus 32. Further radioactive isotopes used to manufacture seeds are not limited to these examples, but can include other sources of different types of radiation. In addition it is to be understood that other types of seeds can be used. In particular, seeds such as those described in U.S. Pat. No. 6,248,057, which patent is incorporated herein by reference and which is entitled Absorbable Brachytherapy and Chemotherapy Delivery Devices and Methods, can be used with the present invention. These seeds include radiation delivery devices, drug delivery devices, and combinations of radiation and drug delivery devices in the form of beads, seeds, particles, rods, gels, and the like. These particular seeds are absorbable wherein the radiation element or drug delivery element is contained within, for example, absorbable polymers such as those listed below or in the above-referenced patent. In such seeds, the bio-absorbable structure can have a predefined persistence which is substantially longer than a half life of the radioactive element contained in the bio-absorbable structure. These above bio-absorbable seeds can be used in the same manner as the seeds described herein with respect to the invention.

The substantially axially, semi-rigid, and radially flexible elongated member may be made of any of the natural and/or synthetic bio-compatible and bio-absorbable materials. Natural and synthetic polymers and copolymers can be used. Examples of synthetic bio-absorbable polymer materials are the polymers and copolymers of glycolide and lactide, polydioxanone and the like. Such polymeric materials are more fully described in U.S. Pat. Nos. 3,565,869, 3,636,956, 4,052,988 and European Patent Application 30822 all of which are incorporated herein by reference. Specific examples of bio-absorbable polymeric materials that can be used to produce the substantially axially stiff and radially flexible elongated member of embodiment of the present invention are polymers made by ETHICON, Inc., Somerville, N.J., under the trademarks "MONOCRYL" and "MAXON" which material is incorporated herein by reference.

Table 2 below provides examples of polymers (and manufacturers) suitable for use in producing embodiments the therapeutic member of the invention. A further discussion of such biodegradable polymers can be found in an article by John C. Middleton and Arthur J. Tipton entitled "Synthetic Biodegradable Polymers as Medical Devices," published March 1998 in Medical Plastics and Bio-materials which article is incorporated herein by reference.

TABLE 2

Biodegradable polymers, properties and degradation time.

| POLYMER | MELTING POINT (° C.) | GLASS-TRANSITION TEMP (° C.) | MODULUS (Gpa)[a] | DEGRADATION TIME (MONTHS)[b] |
|---|---|---|---|---|
| PGA | 225–230 | 35–40 | 7.0 | 6 to 12 |
| LPLA | 173–178 | 60–65 | 2.7 | >24 |
| DLPLA | Amorphous | 55–60 | 1.9 | 12 to 16 |
| PCL | 58–63 | (−65)–(−60) | 0.4 | >24 |
| PDO | N/A | (−10)–0 | 1.5 | 6 to 12 |
| PGA-TMC | N/A | N/A | 2.4 | 6 to 12 |
| 85/15 DLPLG | Amorphous | 50–55 | 2.0 | 5 to 6 |
| 75/25 DLPLG | Amorphous | 50–55 | 2.0 | 4 to 5 |
| 65/35 DLPLG | Amorphous | 45–50 | 2.0 | 3 to 4 |
| 50/50 DLPLG | Amorphous | 45–50 | 2.0 | 1 to 2 |

[a]Tensile or flexural modulus.
[b]Time to complete mass loss. Rate also depends on part geometry.

The final hardness of the polymer of elongate member should preferably be in a range from 20 to 80 durometer and more preferably in the range of 20-40 durometer. The bio-absorbable material should preferably be absorbed in living tissue in a period of time of from about 70 to about 120 days, but can be manufactured to be absorbed anywhere in a range from 1 week to 1 year, depending on the therapeutic plan for each specific patient. Preferably the bio-absorbable material is selected to absorb about when the half-life of the radioactive seeds is reached.

The member or strand is fashioned with a manufacturing method known as insert or compression molding. The radioactive seeds are placed into a fixture that spaces the seeds at the appropriate intervals in a cavity that is shaped to the desired final dimensions of the elongated member. All the spacings can be of different lengths, if the preoperative therapeutic plan so specifies. The synthetic polymer is introduced into the mold at a temperature that is above the melt point of the polymer. The polymer flows around the seeds within the cavity, surrounds the seeds and fills in the spaces between the seeds. After the mold has cooled, it is disassembled, and the finished elongated member is removed. Because the polymer flows at temperatures significantly greater than 250° F., the therapeutic element can easily be steam sterilized before implantation.

As specified above, the elongated member encapsulating radioactive seeds may be fashioned using compression molding techniques. Compression molding forms the molded piece in a two part mold where the polymer material is placed within the cavities of the mold in a liquid state. The seeds are placed in position within the cavities filled with the polymer and the mold is closed and compressed, then cooled to form a piece that conforms to the shape of the closed cavity.

The strand can also be fashioned from two half-shells made from the same material described above. The member or strand is fashioned by sealing the seed elements between the two elongate half-shells and fusing the half-shells by heat or some other method. The seed elements can be placed within two half-shells and liquid material or polymer can be flowed into the center of the unassembled or assembled half-shells, filling all space not occupied by seed elements or spacers.

The seed strand can also be fashioned by producing a catheter or hollow member by extrusion. The material or polymer is placed into a chamber having a die and a mandrel. Pressure is applied by a piston in order to push the material through an opening between the die and the mandrel. During this process, the opening of the die forms the template for the outer wall of the catheter while the mandrel forms the interior bore. The radioactive seeds may then be inserted into the bore of the catheter during the extrusion process or thereafter. The radioactive seeds may be spaced at variable intervals specific to the treatment goals of the end user. All the spacings can be of different lengths, if the preoperative therapeutic plan so specifies.

The manufacturing process also can make the member echogenic. In the case of the molding of the elongated member, air can be entrapped in the polymer material. During the cooling stage of the molding process, the mold is placed in a vacuum chamber and the air in the chamber is evacuated. This causes the entrapped air in the mold to come out of solution from the polymer, and as the mold cools, this air is entrapped within the cooling polymer in the form of minute bubbles suspended in the plastic.

Air is a strong reflector of ultrasound energy, since the inherent impedance of air is many times greater than body tissue. When the elongated member is introduced into the body and imaged with ultrasound, the elongated member is clearly visible in the resulting image, and is thus echogenic.

The resulting elongated member is now a single solid monofilament of the polymer with the seeds spaced within the monofilament and encapsulated at the appropriate intervals. The member is generally very radially flexible such that it can be bent back upon itself in a circle without kinking. However, the member has sufficient column strength along its longitudinal axis so that the member can be urged out of a hollow needle without the member folding upon itself. Again, the intervals can be selected to be any distance or combination of distances that are optimal for the treatment plan of the patient.

Based on the above it is evident that the present invention provides for an embodiment having an elongated member which is comprised of a biodegradable polymer which encapsulates a plurality of spaced radioactive therapeutic seeds. The seeds can be spaced in custom manner so that each member or strand is designed for the particular patient. That is to say that the spacing between each seed pair in a strand or member can be different for each seed pair. Further each individual strand can have an entirely different seed spacing pattern than the next strand or member. Characteristically or typically for a surgical procedure, up to twenty-five of such strands or members are used to encircle the organ or tumor that is affected.

Further such an arrangement provides for a strand or member that is stiff along its longitudinal axis. That is to say that the strand or member has column strength or stiffness while the strand or member is flexible in the direction which is radial or substantially perpendicular to the longitudinal axis. Accordingly the strand or member in a preferred embodiment is able to bend back upon and touch itself, when formed in a characteristic length.

In other embodiments, the strand or member can be made with the incorporation of drugs and/or hormones and/or other therapeutics which are embedded in or formed in the polymer and/or seeds. Thus the embodiment of the invention can deliver not only radioactive seeds, but such therapeutic drugs, hormones and other therapeutic devices. In addition the strand or member can deliver heated seeds such as provided by ATI Medical. Then seeds can be preferably heated to from about six (6) degrees centigrade to about seventy (70) degrees centigrade prior to being inserted into a patient in a preferred embodiment. ATI Medical is located at (www.ATImedical.com), and reference to such heated seeds is incorporated herein by reference.

It should be understood that other seed types can be used with the present invention. Thus for example in addition to the above encapsulated seeds, seeds which are made of radioactive or coiled wires can be embedded in the polymer and be within the spirit and scope of the invention. These seeds can be individual seeds which are spaced within a polymer or a continuous seed which extends the length of the strand or member.

Figure 3:
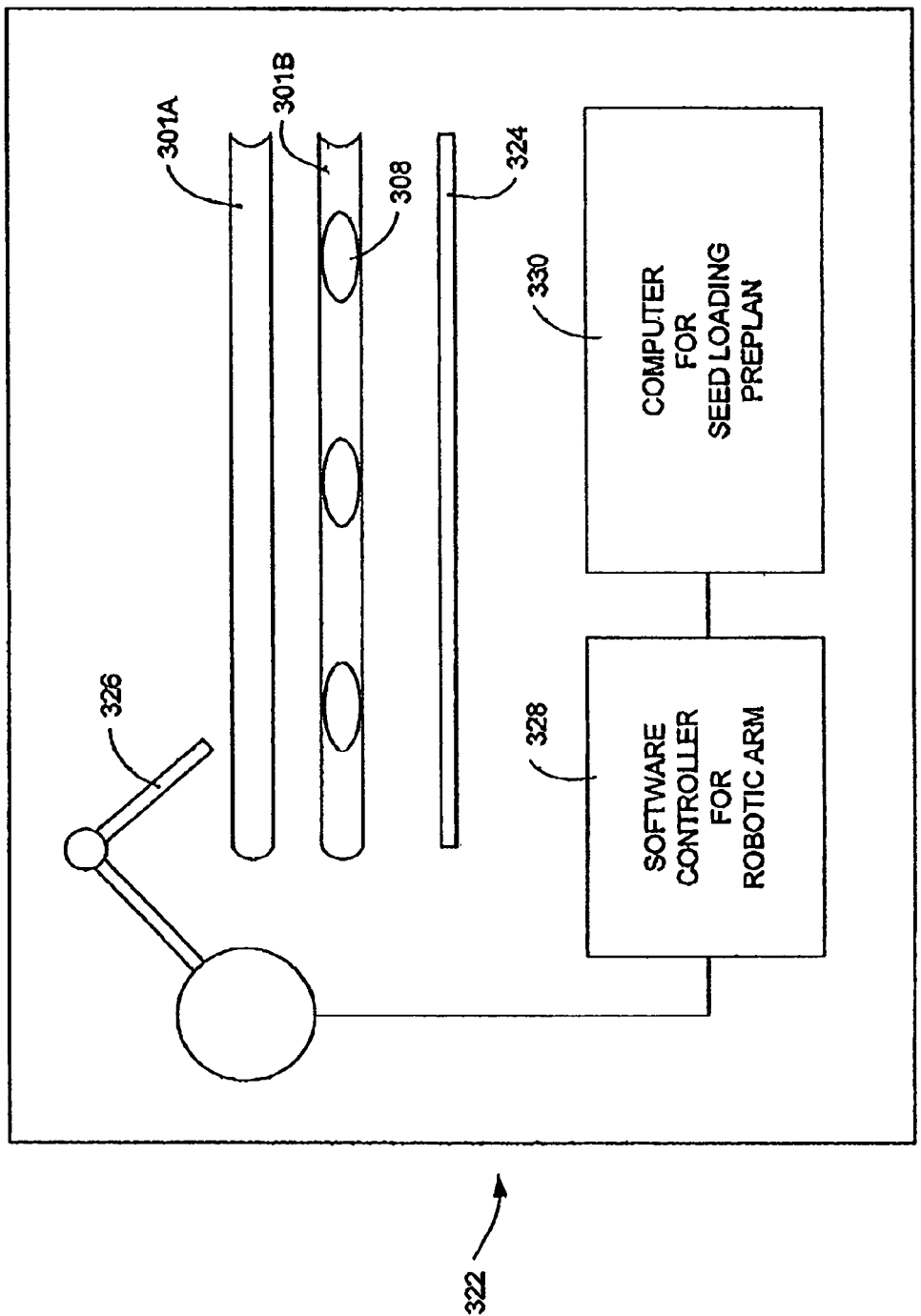
FIG. 3 is a schematic of an embodiment of a system for manufacturing interstitial radiation therapy seed strands of the invention.

Further to the invention, as discussed above, it should be understood that the strand or member can be made echogenic by the incorporation of, for example, air bubbles 32 in the polymer spaces between the seeds, as can be seen in FIGS. 1 and 3. These air bubbles or pockets can be formed in the polymer in ways identified above and other ways known to one of skill in the art.

According to the above, the advantages of the improved delivery system submitted of the present invention are:

1. The substantially axially stiff and radially flexible elongated member allows controlled placement of the plurality of radioactive seeds that are encapsulated and positioned in a predetermined array in the member without migration of the individual radioactive seeds during the time the seeds are treating the tumor.

2. The fixed linear positioning of the seeds minimizes "hot" and "cold" radiation spots due to undesirable movement of the seeds.

3. The normal tissue is spaced away from the seed surface by the thickness of the body of polymer, to decrease necrosis from a high local dose.

4. The axial stiffness of the elongated member allows the elongated member to be urged out of the needle as the needle is withdrawn, without the member jamming in the needle, by collapsing or expanding as the needle is withdrawn from the tumor site.

5. The radial flexibility of the elongated member allows locational accuracy to be maintained as the gland shrinks to pre-procedural size, as the swelling that occurs during tissue disruption and needle manipulation recedes.

6. Increased speed of implant resulting in reduced surgical time and health care provider radiation exposure.

Method of Delivering Customized Strands and/or Members Per a Therapeutic Prescription As is known in the industry, there is software which can be used to provide branchytherapy treatment planning guides which are customized for each individual patent. Such software is provided by Rossmed which is located at Ross Medical, 7100 Columbia Gateway Drive, Suite 160, Columbia, Md. 21046. This particular software, which is incorporated herein by reference, is known as the Strata suite, which software helps physicians to develop and visualize low dose rate brachytherapy treatment plans for treating malignant tumors in human tissue. The treatments entail the use of radioactive seed sources which are implanted adjacent to the malignant tissue. The Strata software uses imaging to create a three dimensional reconstruction of the patient's anatomy. The software is able to plan the placement of the seeds within the target. The radiation dose that is delivered to the target can be computerized and visualized using the software. The software can then specify an optimal number of strands or members along with optimal seed dosages and spaces between seeds. At times the loading plans so specified cannot be optimized by the physician in preparing the seed and spacer loads for the needles, as the spacers come in only predefined lengths.

Accordingly with the present invention, the software can be used to prepare a prescription which optimizes the number of members or strands, and placement and spacing of seeds for each of the strands or members. This optimization plan can then be sent to a manufacturing site. By using the techniques of an embodiment of the present invention, an optimized strand or member can be created with the specified number of seeds and the specified distances between each seed pair. Once this prescription is filled at the manufacturing site, the custom strand or member can be sent back to the physician for treatment of the patient. With such an arrangement, radiation patterns can be optimally established for the treatment of each patient. Further the preparation time for the physician is greatly diminished as the physician does not have to hand assemble and hand load the seeds and spacers into the needle.

Further even if the physician were to use a prescription provided by the above software, with prior manufacturing techniques, the physician would only receive from the manufacturing facility a strand or member which has seeds spaced at predefined intervals, which are the lengths or the pre-manufactured spacers. Accordingly optimal treatment as provided by the custom strands or members manufactured according to the present invention could not be realized.

The Embodiments of FIGS. 1A through 1C Represent a Delivery System and Method for Interstitial Radiation Therapy In FIG. 1A, the therapeutic elongated element or member or matrix or strand 104 is displayed having the semi-rigid, radially flexible polymer 106 and the radioactive seeds 108. As can be seen in FIG. 1A, the polymer fills the spacing segments 110 in a contiguous manner to fashion the total elongate member.

FIG. 1C shows a side view of the brachytherapy device 112. The needle 114 is shown partially broken away and has a sheath component 116, and is loaded with the therapeutic element or member 104. The beveled end 118 of the needle 114 is plugged with a bio-compatible substance 120. The plug prevents fluids and tissue from entering the needle and coming in contact with the member 104 prior to the placement of the member or strand 104 adjacent the tumor. The plug 120 can be made out of a bone wax or can be made of one of the bio-absorbable polymers or copolymers listed herein. Further the plug can be the end of the member or strand 104 that is heated and reflowed after the strand or member is inserted into the needle. A stylet or stylus 122 is inserted into the needle until it meets the therapeutic element or member 104. Then the needle 114 is inserted into the site and the therapeutic member 104 is gradually extruded from the needle via the static force of the stationary stylus 122, as the needle 114 is pulled back.

The Embodiments of FIGS. 2A through 2E Represent a Interstitial Radiation Therapy Seed Strands Constructed with Half-Shell Strand Housings In FIG. 2A, the elongated members shaped like half-shells 201A, B are shown. The elongate members 201A, B may be composed of a bioabsorbable material such as previously described and such as previously listed in Table 2. The seed elements 208 and spacers 209 are placed within one of the half-shells 201A. Seed elements 208 can be coated with or contain any low energy short half-life radioisotope, such as previously listed in Table 1, and/or a drug and/or hormone. The half-shells 201A, B can then be mated, containing the seed elements 208 and spacers 209 as shown in FIG. 2A. To form the therapeutic element, the half-shells 201A, B are then heated, fusing the half-shells 201A, B and fixing the seed elements 208 and spacers 209 inside.

Alternatively, a bioabsorbable material can be flowed into the half-shell having appropriate spaced seeds and without spaces (FIG. 2C). The flowed in bioabsorbable materials maintains the appropriate spacing. As the bioabsorbable material is flowed in, the seeds are maintained in position by manufacturing fingers or by being urged into the material of the half-shell. After the material is flowed in, the two half-shells are assembled and if required, heated to form the final assembly. Also it is understood that a polymer can be flowed into a half shell prior to the assembly of the two half shells, together. Thereafter, the two half shells can be assembled and heated, if required, for fusing the assembly together.

FIG. 2D shows a side view of elongate solid member half-shells 201 with indentations 210 for seed elements 208. The indentations can have a variety of shapes from those that follow the contour of the seeds to other shapes such as, for example, the rectangular shapes. The half-shells 201 are composed of material as described with respect to FIGS. 1A to 1C. The seed elements are also described with respect to FIGS. 1A to 1C. The seed elements 208 are placed into the indentations 210 and the two half-shells 201 mated. The half-shells 201 are then fused by heating or other means, fixing the seed elements 208 inside and forming the therapeutic element.

Figure 2E:
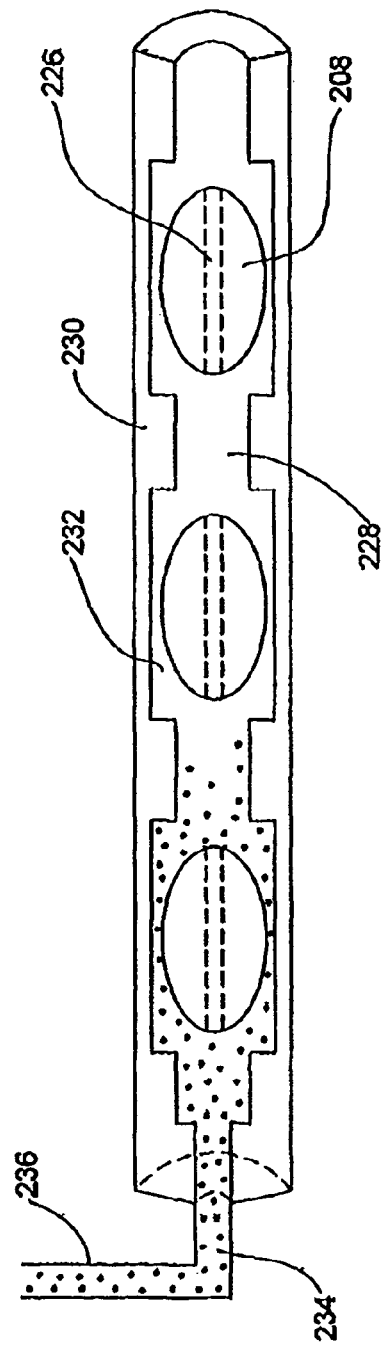
FIG. 2E is an enlarged side view of two mated half-shells with seed elements placed in indentations and a liquid material flowing into the spaces around and between the seed elements within the mated half-shells.

FIG. 2E shows a side view of a method of making a therapeutic element. Two half-shells 201 have been mated with seed elements 208 inside. The half-shells 201 and seed elements 208 are described above in FIGS. 2A-2D. The half-shells 201 have indentations 232 for the seed elements 208 and remaining dead space 228 between the seed elements 208. The seed elements 208 can be held tightly in the indentations 232 of the assembled half-shells 201, and as such, the seed elements 208 have holes 226 through their centers to allow material 234 to flow through the entire strand. Material 234 is injected into the mated half-shells 201 via a device 236 and the material 234 fills all the remaining space in the indentations 232 and dead space 228 between the seed elements 208. The therapeutic element is formed when the material 234 solidifies, fusing the half-shells 201 and fixing the seed elements 208 in place within the therapeutic element. Upon solidifying, the material 234 is axially rigid and radially flexible and may be bioabsorbable or composed of any of the polymers listed in Table 2. Alternatively, solid seeds can be used with some space being present between the seeds and indentation in the assembled preformed half shell. The indentations keep the seeds in place and allow the polymer to flow past the seeds. Alternatively, the indentations can have fingers that keep the seeds from touching the walls of the indentations of the half shells. The polymer can thus flow into the bore of the assembled half shells and past the fingers.

The Embodiment of FIG. 3 is a System for Manufacturing Radiation Therapy Seed Strands In FIG. 3, a schematic of one embodiment of the present invention is shown. The pictured components of the system 322 are not necessarily proportional to each other. The embodiment uses first and second elongate half-shell members 301A, 301B. The elongate half-shell members 301A, 301B may be composed of any material that is axially rigid and radially flexible when assembled with seeds into a strand. Such a material may be a bioabsorbable polymer selected from those listed above and also in Table 2. Within the second half-shell elongate member 301B is positioned seed elements 308. The seed elements can be spread with the same or different intervals as required for treating the patient. The seed elements 308 may be coated with or contain a low energy, short half-life radioisotope such as those listed above and also in Table 1. The seed elements 308 may also be coated with or contain a drug or hormone. Alternatively, the seed elements 308 can, at least in part, be constructed of a bioabsorbable material. A heating element 324 is also depicted. A computer 330 is connected to a robotic arm controller 328, which operates a robotic arm 326.

To manufacture a seed strand, the computer 330 processes a seed loading protocol based on a treatment plan specific to the patient as described above. The computer 330 then communicates with the controller 328 which controls the robotic arm 326. Based upon this information, the robotic arm 326 picks the seed elements 308 according to the treatment plan and seed loading protocol and places the seed elements 308 in one half-shell elongate member 301B. Then the robotic arm 326 or another robotic arm (not shown) picks up the other elongate half-shell member 301A and mates it to the elongate member 301B containing the seeds. Next, the robotic arm 326 places the half-shell assembly 301A,B containing the seed elements 308 into a heating element 324 where the half-shells 301A,B are heated and fused, fixing the seed elements 308 in place. Alternatively, liquid material can be injected in 301A, B, whether the half shells are assembled or unassembled, and around the seed elements 308 using techniques described above. When the material solidifies, it fuses the half-shells 301A,B, fixing the seed elements 308 in place, and the assembly is axially rigid and radially flexible.

The system 322 can also provide a facility to test each of the seeds. The system 322 can be compact and if desired be configured as a table-top unit which can be located at a hospital or other treatment site and manufacture seed strands as they are needed for a patient. Based on the above it is evident that the present invention provides for a system and method for manufacturing interstitial radiation therapy strands that produce an elongated member which is comprised of a biodegradable polymer which encapsulates a plurality of spaced radioactive therapeutic seeds. The seeds can be spaced in a custom manner so that each member or strand is designed for the particular patient. That is to say that the spacing between each seed pair in a strand or member can be different for each seed pair. Further each individual strand can have an entirely different seed spacing pattern than the next strand or member.

Figure 4A:
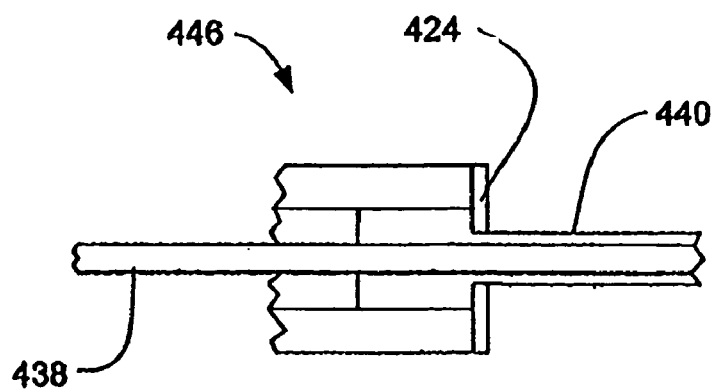
FIG. 4A is an enlarged side view of an embodiment of the invention for extruding a seed housing in the shape of a tube.
Figure 4B:
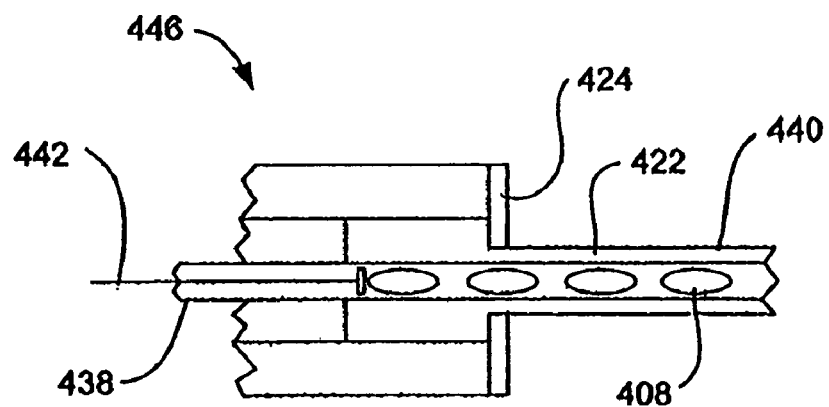
FIG. 4B is an enlarged side view of the device in FIG. 4A with a component seed loader.
Figure 4C:
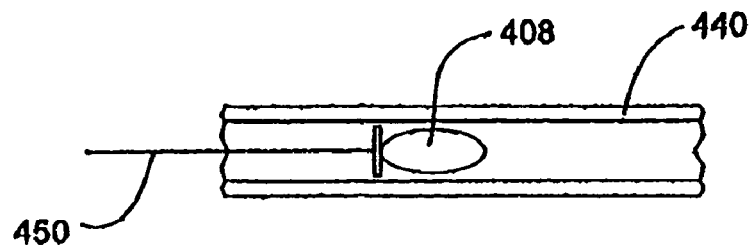
FIG. 4C is an enlarged side view of an embodiment the seed loader of the invention for use with the seed housing of FIG. 4A.

The Embodiment of FIGS. 4A through 4C is a System for Manufacturing Radiation Therapy Seed Strands Using Extruded Strand Housings FIG. 4A depicts a system 446 for forming a seed housing in the shape of a tube and of, in this particular embodiment, a bioabsorbable polymer as described above. The system 446 includes a mandrel 438, a piston 444 and a die 424. As the piston extrudes the material 440 over the mandrel 438 and through the die 424, an elongate hollow member or seed housing is formed that is shaped like a catheter. The resulting interstitial radiation therapy device is much longer than its width. The width of such a device should be narrow enough to be accommodated into a needle for implantation into the treatment site as described above. In its final state assembled with seeds, the material 440 must be axially rigid and radially flexible and can be any of the polymers listed in Table 2 above. The material 440 may also be bioabsorbable.

FIG. 4B shows the extrusion apparatus from FIG. 4A with seed elements 408 and modified to have a seed pusher 442. The material 440 is extruded through the opening of the die 424 by pressure from the polymer pusher 438 forming a catheter or seed housing with a bore. A seed pusher 442 then inserts seed elements 34 into the bore of the catheter at the desired location. The seed elements 408 may be coated or contain any low energy, short half life radioisotope such as those listed in Table 1 above. The seed elements 408 may also be coated with or contain a drug or hormone. The seed elements 408 may be composed of a radio-opaque metal such as titanium or a bioabsorbable polymer.

FIG. 4C shows a seed pusher 450 as it inserts a seed element 408 to the desired location into the bore of the seed housing that had been previously extruded in accordance with FIG. 4A. For all the methods and devices discussed above and depicted, the spacing between seeds or capsules containing seeds can be optimized and custom set between seed or capsule pairs per a prescription treatment plan.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed is:

1. A method for providing a treatment strand for use in brachytherapy, comprising:
   (a) accepting a custom prescription tissue treatment plan specifying the spacing of a plurality of treatment seeds to be provided in a treatment strand for treating tissue of a patient, wherein the spacing of adjacent, non-abutting treatment seeds is specified along a longitudinal axis of the treatment strand and is not defined by one or more spacers or seeds;
   (b) providing instructions for preparing the treatment strand to an automated loader based on the custom prescription tissue treatment plan; and
   (c) preparing the treatment strand by positioning treatment seeds in an elongate member by introducing the treatment seeds to at least one end of the elongate member using the automated loader and urging the treatment seeds along the longitudinal axis from the at least one end to a prescribed position in the elongate member based on the provided instructions; and wherein the elongate member includes a polymer material that is radially flexible and axially stiff.

2. The method of claim 1, wherein the elongate member comprises an extruded tube.

3. The method of claim 1, wherein the treatment seeds comprise radioactive seeds.

4. The method of claim 1, wherein the treatment strand made from the elongate member has sufficient column strength along its longitudinal axis so that it can be urged out of a needle during implantation without folding upon itself, and has sufficient radial flexibility such that it can flex following implantation, thereby enabling the strand to maintain implanted location accuracy as patient tissue swells and shrinks.

5. The method of claim 1, wherein the elongate member includes a bioabsorbable material.

6. The method of claim 1, further comprising:
  (a1) processing a seed loading protocol based on the custom prescription tissue treatment plan; and
  (a2) generating instructions for preparing the treatment strand based on the seed loading protocol.

7. A system for providing a treatment strand for use in brachytherapy, comprising:
  means for accepting a custom prescription tissue treatment plan specifying the spacing of a plurality of treatment seeds to be provided in a treatment strand for treating tissue of a patient, wherein the spacing of adjacent, non-abutting treatment seeds is specified along a longitudinal axis of the treatment strand and is not defined by one or more spacers or seeds;
  means for generating instructions for preparing the treatment strand based on the custom prescription tissue treatment plan; and
  an automated seed pusher to execute the instructions to place treatment seeds in a radially flexible and axially stiff elongate polymer member by introducing the treatment seeds to at least one end of the elongate member and urging the treatment seeds along the longitudinal axis from the at least one end to a prescribed position in the elongate member so that the seeds are spaced apart from one another in accordance with the custom prescription treatment plan.

8. The system of claim 7, wherein the elongate member remains radially flexible and axially stiff as the seed pusher pushes the treatment seeds into the at least one end of the elongate member.

9. The system of claim 7, wherein the elongate member remains radially flexible and axially stiff after the seed pusher pushes the treatment seeds into the at least one end of the elongate member.

10. The system of claim 7, wherein an outer diameter of the elongate member is generally the same before and after the seed pusher pushes the treatment seeds into the at least one end of the elongate member.

11. A method for providing a treatment strand for use in brachytherapy, comprising:
  (a) accepting a custom prescription tissue treatment plan specifying the spacing of a plurality of treatment seeds to be provided in a treatment strand for treating tissue of a patient, wherein the spacing of the plurality of treatment seeds is specified along a longitudinal axis of the treatment strand and is not defined by one or more spacers;
  (b) providing instructions for preparing the treatment strand to an automated loader based on the custom prescription tissue treatment plan; and
  (c) preparing the treatment strand by positioning treatment seeds in an elongate member by introducing the treatment seeds to at least one end of the elongate member using the automated loader and urging the treatment seeds along the longitudinal axis from the at least one end to a prescribed position in the elongate member based on the provided instructions;
    wherein urging the treatment seeds includes using a seed pusher to push the treatment seeds into the at least one end of the elongate member so that a spacing between a pair of the seeds is different than a spacing between another pair of the seeds; and
    wherein the elongate member includes a material that is radially flexible and axially stiff.

12. The method of claim 11, wherein the elongate member remains radially flexible and axially stiff as the seed pusher pushes the treatment seeds into the at least one end of the elongate member.

13. The method of claim 11, wherein the elongate member remains radially flexible and axially stiff after the seed pusher pushes the treatment seeds into the at least one end of the elongated hollow member.

14. The method of claim 11, wherein an outer diameter of the elongate member is generally the same before and after the seed pusher pushes the treatment seeds into the at least one end of the elongate member.

15. The method of claim 11, wherein the elongate member includes a bioabsorbable material.

16. The method of claim 11, wherein the elongate member comprises an extruded tube.

17. The method of claim 11, wherein the treatment seeds comprise radioactive seeds.

18. The method of claim 11, wherein the treatment strand made from the elongate member has sufficient column strength along its longitudinal axis so that it can be urged out of a needle during implantation without folding upon itself, and has sufficient radial flexibility such that it can flex following implantation, thereby enabling the strand to maintain implanted location accuracy as patient tissue swells and shrinks.

19. The method of claim 11, wherein the elongate member includes a bioabsorbable material.

20. A method for providing a treatment strand for use in brachytherapy, comprising:
  (a) accepting a custom prescription tissue treatment plan specifying the spacing of a plurality of treatment seeds to be provided in a treatment strand for treating tissue of a patient, wherein the spacing of adjacent, non-abutting treatment seeds is specified along a longitudinal axis of the treatment strand and is not defined by one or more spacers or seeds;
  (b) providing instructions for preparing the treatment strand to an automated loader based on the custom prescription tissue treatment plan; and
  (c) preparing the treatment strand by introducing the treatment seeds to at least one end of an elongate polymer member and urging the treatment seeds along the longitudinal axis from the at least one end to a prescribed position in the elongate member based on the provided instructions.

21. The method of claim 20, wherein the elongate member comprises an extruded tube.

22. The method of claim 20, wherein the treatment seeds comprise radioactive seeds.

23. The method of claim 20, wherein the treatment strand made from the elongate member has sufficient column strength along its longitudinal axis so that it can be urged out of a needle during implantation without folding upon itself, and has sufficient radial flexibility such that it can flex following implantation, thereby enabling the strand to maintain implanted location accuracy as patient tissue swells and shrinks.

24. The method of claim 20, wherein the elongate member is formed from a bioabsorbable material.

25. The method of claim 20, further comprising:
(a1) processing a seed loading protocol based on the custom prescription tissue treatment plan; and
(a2) generating instructions for preparing the treatment strand based on the seed loading protocol.

26. A method for providing a treatment strand for use in brachytherapy, comprising:
(a) accepting a custom prescription tissue treatment plan specifying the spacing of a plurality of treatment seeds to be provided in a treatment strand for treating tissue of a patient, wherein the spacing of the plurality of treatment seeds is specified along a longitudinal axis of the treatment strand and is not defined by one or more spacers;
(b) providing instructions for preparing the treatment strand to an automated loader based on the custom prescription tissue treatment plan;
(c) preparing the treatment strand by introducing the treatment seeds to at least one end of the elongate member and urging the treatment seeds along the longitudinal axis from the at least one end to a prescribed position in the elongate member based on the provided instructions; and
wherein urging the treatment seeds includes using a seed pusher to push the treatment seeds into the at least one end of the elongate member so that a spacing between a pair of the seeds is different than a spacing between another pair of the seeds.

27. The method of claim 26, wherein the treatment seeds comprise radioactive seeds.

28. The method of claim 26, wherein the treatment strand made from the elongate member has sufficient column strength along its longitudinal axis so that it can be urged out of a needle during implantation without folding upon itself, and has sufficient radial flexibility such that it can flex following implantation, thereby enabling the strand to maintain implanted location accuracy as patient tissue swells and shrinks.

29. The method of claim 26, wherein the elongate member is formed from a bioabsorbable material.

30. The method of claim 26, further comprising:
(a1) processing a seed loading protocol based on the custom prescription tissue treatment plan; and
(a2) generating instructions for preparing the treatment strand based on the seed loading protocol.

31. The method of claim 26, wherein the treatment seeds comprise radioactive seeds.

32. The method of claim 26, wherein the elongate member includes a bioabsorbable material.

33. A system for providing a treatment strand for use in brachytherapy, comprising:
means for accepting a custom prescription tissue treatment plan specifying the spacing of a plurality of treatment seeds to be provided in a treatment strand for treating tissue of a patient, wherein the spacing of adjacent, non-abutting treatment seeds is specified along a longitudinal axis of the treatment strand and is not defined by one or more spacers or seeds;
means for generating instructions for preparing the treatment strand based on the custom prescription tissue treatment plan; and
an automated seed pusher to execute the instructions to place treatment seeds in an elongate polymer member by introducing the treatment seeds to at least one end of the elongate member and urging the treatment seeds along the longitudinal axis from the at least one end to a prescribed position in the elongate member so that the seeds are spaced apart from one another in accordance with the custom prescription treatment plan.

34. A method for providing a treatment strand for use in brachytherapy, comprising:
(a) accepting a custom prescription tissue treatment plan specifying the spacing of a plurality of treatment seeds to be provided in a treatment strand for treating tissue of a patient, wherein the spacing of adjacent, non-abutting treatment seeds is specified along a longitudinal axis of the treatment strand and is not defined by one or more spacers or seed;
(b) providing the custom prescription tissue treatment plan to an automated loader; and
(c) preparing the treatment strand by positioning treatment seeds in an elongate polymer member by introducing the treatment seeds to at least one end of the elongate member using the automated loader and urging the treatment seeds along the longitudinal axis from the at least one end to a prescribed position in the elongate member based on the provided instructions; and
wherein the elongate member includes a material that is radially flexible and axially stiff.

* * * * *

UNITED STATES PATENT AND TRADEMARK OFFICE
CERTIFICATE OF CORRECTION

PATENT NO. : 8,066,627 B2
APPLICATION NO. : 11/455305
DATED : November 29, 2011
INVENTOR(S) : Terwilliger et al.

It is certified that error appears in the above-identified patent and that said Letters Patent is hereby corrected as shown below:

Col. 3, line 46, before "for bead strands", change "devices" to "device"

Col. 5, line 57, after "half-shell into which", change "has" to "have"

Col. 5, line 58, after "solidify", change "at" to "as"

Col. 6, line 5, after "accurately", change "spaces" to "spaced"

Col. 7, line 4, before "on a silver rod", change "absorbed" to "adsorbed"

Col. 11, line 5, after "used to provide", change "branchytherapy" to "brachytherapy"

Col. 11, line 6, after "individual", change "patent" to "patient"

Signed and Sealed this
Twenty-fifth Day of September, 2012

David J. Kappos
*Director of the United States Patent and Trademark Office*